(12) United States Patent
Schwarz et al.

(10) Patent No.: US 10,058,508 B2
(45) Date of Patent: Aug. 28, 2018

(54) DIRECT COMPRESSION EXCIPIENT BASED ON LACTOSE, CELLULOSE AND STARCH

(71) Applicant: Molkerei MEGGLE Wasserburg GmbH & Co. KG, Wasserburg (DE)

(72) Inventors: Eugen Schwarz, Wasserburg (DE); Vera Fichtner, Reitmehring (DE)

(73) Assignee: MOLKEREI MEGGLE WASSERBURG GMBH & CO. KG, Wasserburg (DE)

( * ) Notice: Subject to any disclaimer, the term of this patent is extended or adjusted under 35 U.S.C. 154(b) by 37 days.

(21) Appl. No.: 15/515,171

(22) PCT Filed: Sep. 29, 2015

(86) PCT No.: PCT/EP2015/072420
§ 371 (c)(1),
(2) Date: Mar. 29, 2017

(87) PCT Pub. No.: WO2016/050768
PCT Pub. Date: Apr. 7, 2016

(65) Prior Publication Data
US 2017/0216209 A1    Aug. 3, 2017

(30) Foreign Application Priority Data
Sep. 30, 2014   (EP) .................................. 14187045

(51) Int. Cl.
*A61K 9/16* (2006.01)

(52) U.S. Cl.
CPC .............. *A61K 9/1652* (2013.01); *A61K 9/16* (2013.01); *A61K 9/1617* (2013.01); *A61K 9/1623* (2013.01)

(58) Field of Classification Search
CPC .......... A61K 9/20; A61K 9/16; A61K 9/1617; A61K 9/1652; A61K 9/1623
See application file for complete search history.

(56) References Cited

U.S. PATENT DOCUMENTS

| | | | |
|---|---|---|---|
| 4,693,750 A * | 9/1987 | Bauer | A61K 9/2018 106/162.9 |
| 4,724,141 A | 2/1988 | Schmidt et al. | |
| 5,855,912 A | 1/1999 | Ortyl et al. | |
| 6,770,368 B2 | 8/2004 | Luhn | |

(Continued)

FOREIGN PATENT DOCUMENTS

| EP | 1062945 A1 | 12/2000 |
|---|---|---|
| EP | 0948321 B1 | 10/2003 |

(Continued)

OTHER PUBLICATIONS

Gohel et al. 2003 Exploration of Melt Granulation Technique for the Development of Coprocessed Directly Compressible Adjuvant Containing Lactose and Microcrystalline Cellulose. Pharmaceutical development and Technology. 2003, vol. 8(2); 175-183.*

(Continued)

*Primary Examiner* — Lakshmi S Channavajjala
(74) *Attorney, Agent, or Firm* — Withers & Keys, LLC

(57) ABSTRACT

The present invention relates to compositions comprising at least one lactose component, at least one cellulose component and at least one starch component, its preparation and its use, particularly as a direct tabletting excipient.

20 Claims, 13 Drawing Sheets

(56) References Cited

U.S. PATENT DOCUMENTS

Figure 1:
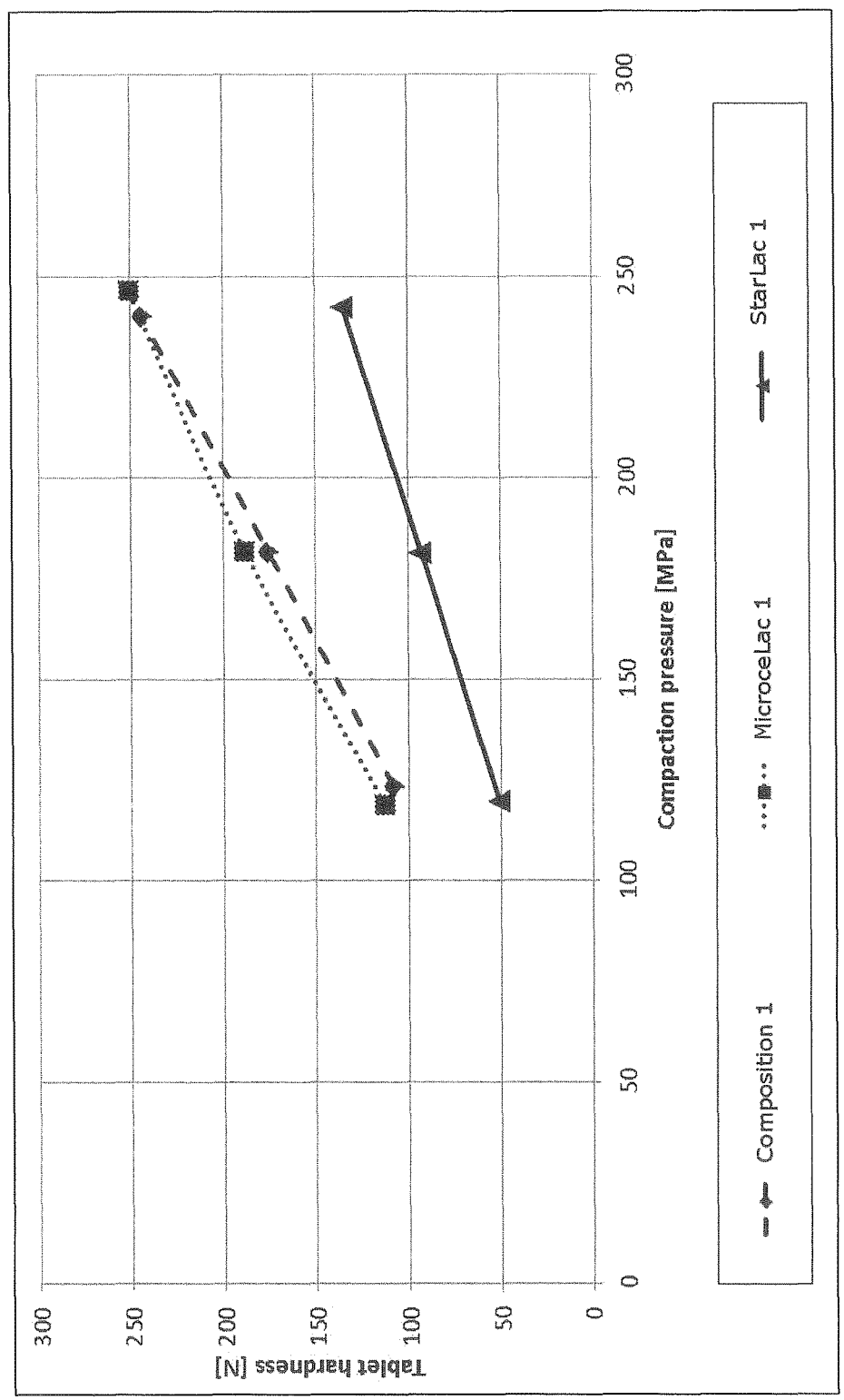

2003/0220403 A1 11/2003 Corvari et al.
2007/0154544 A1 7/2007 Hrakovsky et al.

FOREIGN PATENT DOCUMENTS

| WO | WO 1998025590 A2 | 6/1998 | |
|----|------------------|--------|--|
| WO | WO 2004047798 A2 | 6/2004 | |
| WO | WO 2006068484 A2 | 6/2006 | |
| WO | WO 2007114921 A2 | 10/2007 | |
| WO | WO 2011074961 A1 | 6/2011 | |
| WO | WO-2014082651 A1 * | 6/2014 | ........... A61K 9/2013 |

OTHER PUBLICATIONS

PharmTech.com-2018 Dressler et al. A Corn Starch/a-Lactose Monohydrate Compound as a Directly Compressible Excipient. 2003 . Pharmaceutical Technology Europe, vol. 15(3), 3 pages http://www.pharmtech.com/corn-starcha-lactose-monohydrate-compound-directly-compressible-excipient.*

* cited by examiner

DIRECT COMPRESSION EXCIPIENT BASED ON LACTOSE, CELLULOSE AND STARCH

This application is being filed as the national stage patent application of PCT International Patent Application No. PCT/EP2015/072420, filed on 29 Sep. 2015, and claiming priority to European Patent Application Serial No. 14187045.1, filed on 30 Sep. 2014, and entitled "DIRECT COMPRESSION EXCIPIENT BASED ON LACTOSE, CELLULOSE AND STARCH," the contents of both of which is incorporated herein by reference in its entirety.

The present invention relates to compositions, particularly agglomerates, comprising at least one lactose component, at least one cellulose component and at least one starch component, its preparation and its use, particularly as a direct tabletting excipient.

Tablets are defined from a technological perspective as solid single dosage forms of pharmaceuticals, which are produced by compressing powders and granulates in various forms. The composition of tablets can be extremely diverse and has to be developed individually for each active agent, each intended use and each manufacturing technology.

Typical tablet formulations contain, in addition to the pharmaceutically active component, so-called tabletting excipients, such as fillers (e.g. lactose, cellulose powder and calcium diphosphate), sugar alcohols (e.g. mannitol, sorbitol, Xylitol and malitol), disintegrants (e.g. croscarmellose, crosslinked PVPP, starch and sodium-carboxymethyl cellulose), lubricants (e.g. stearic acid, magnesium stearate), glidants (e.g. silicon dioxide (Aerosil®)) or mixtures thereof. Tabletting excipients are additives that make a practical manufacturing of tablets possible and have an essential influence on the processability of the tablet formulation and on the properties of the finished tablet. The tabletting excipients are selected depending on the pharmacokinetic requirements and the respective active agent.

Usually, the pharmaceutically active agents together with the respective tabletting excipients are manufactured into a granulate with the aid of a solvent (e.g. via wet granulation). Subsequently, the obtained granulate is pressed to form a tablet. However, the simplest and most economical way of manufacturing tablets is direct tabletting, i.e. tabletting without previous granulation of active component(s) and tabletting excipients. Tablet formulations which are suitable for direct tabletting have to have a sufficient plastic deformability and good flow properties and must not exhibit any separation tendencies. Due to these complex requirements, direct tabletting has only rarely been carried out so far (K. Bauer, "Pharmazeutische Technologie", 1993, publisher Georg Thieme, Stuttgart).

Besides cost effectiveness, a further advantage of direct tabletting is that no granulation of the pharmaceutically active component is necessary and therefore solvent-sensitive components can readily be processed to form tablets.

Hence, there is a great demand for tabletting excipients which can simply be mixed with the pharmaceutically active agent and optionally with further tabletting excipients and subsequently be compressed directly (direct tabletting excipient). The property profile of directly compressible tablet formulations described above is in most cases not achieved by simply (physically) mixing the commercially available individual components of a tablet formulation. Therefore, mixed granulates comprising different tabletting excipients are often used.

Such mixed granulates are suitable for the conventional production of tablets and other dosage forms, but may also be advantageous as direct tabletting excipient.

U.S. Pat. No. 6,770,368 describes a granulate consisting of starch and lactose used as excipients for direct tabletting. The granulate is prepared by spray drying a solution or suspension of both components.

U.S. Pat. No. 4,693,750 describes an excipient for direct tabletting, which essentially consists of lactose and cellulose. For this purpose, cellulose powder and lactose are mixed in hot water and subsequently spray dried.

EP 0 948 321 discloses the production of a lactose/ethyl cellulose preparation, wherein both components are dispersed in water by means of a stirrer and subsequently spray dried.

U.S. Pat. No. 6,770,368 concerns granules consisting of lactose and starch. As particularly preferred embodiment, a granulate containing 85% by weight of α-lactose monohydrate and 15% by weight of native maize starch is described. The latter product is commercially available under the tradename StarLac® (Meggle Group, Wasserburg). The granulate is used for direct compression tablet manufacture and is particularly characterized by its rapid disintegration profile. However, the tablet hardness achieved with the StarLac® product might be improved.

Granules made of α-lactose monohydrate (75 wt.-%) and a microcrystalline cellulose (25 wt.-%) are commercially available under the tradename MicroceLac® 100 (Meggle Group, Wasserburg). The granulate is primarily used for direct compression (DC) tablet manufacture and is suitable for providing improved hardness, which can be yielded in the tablets produced therewith. Although MicroceLac® provides excellent tablet hardness, the disintegration times are to be improved.

WO 2011/074961 deals with co-processed excipient compositions comprising granules, said granules comprising at least one filler-binder and at least one lubricant which have been subjected to granulation together, said granules being coated with lactose. It was found that flowability can be increased without sacrificing disintegration. The developed excipient is said to have overcome the obligatory final coating of excipients with lubricants which complicates tablet manufacture and loss of compactability.

There was a long-lasting need of direct tabletting excipients that exhibit a good flowability while simultaneously having a high hardness yield and fast disintegration times. Such a performance is requested for a variety of drug containing tablets e.g. for analgetics.

Thus, in one aspect, the present invention provides a composition comprising at least one lactose component, at least one cellulose component and at least one starch component.

Lactose belongs to the group of disaccharides and consists of the two molecules β-D-galactose and α/β-D-glucose, which are linked together by a β-1,4 glycosidic bond. According to the invention, the lactose component may be an anhydrous lactose or a lactose monohydrate. Lactose monohydrate is preferred, since it is less hygroscopic compared to anhydrous lactose and is thus more suitable in compositions containing water-sensitive pharmaceutically active components.

Cellulose is a polysaccharide composed of a large number of β-D-glucose molecules, which are linked by a 1,4-β glycosidic bond. The hydroxyl groups present in the polysaccharide can be chemically modified in a variety of ways. The hydroxyl groups of cellulose can, independently of each other, be at least partially alkylated, hydroxy alkylated, sulfonated, nitrated, carboxy alkylated or/and xanthogenated under certain reaction conditions. The modified celluloses obtained are defined as "cellulose derivatives", whose profile of properties, e.g. with regard to water-solubility and active substance compatibility, can be tailored for the respective applications. According to the invention, the cellulose component may be selected from celluloses such as microcrystalline cellulose (MCC) and powder cellulose and cellulose derivatives such as hypromellose (hydroxypropyl methyl cellulose (HPMC)), hydroxypropyl cellulose (HPC), hydroxyethyl cellulose (HEC), carboxymethyl cellulose (CMC), carboxyethyl cellulose (CEC), ethyl cellulose (EC), hypromellose phthalate, and salts thereof. In preferred embodiments, the cellulose component is a microcrystalline cellulose (MCC), preferably having a molecular weight of 20.000 to 50.000 Da, more preferably of 32.000 to 39.000 Da.

Starch is a carbohydrate consisting of a large number of glucose units joined by glycosidic bonds. The polysaccharide is contained in large amounts in e.g. potatoes, sweet maize (corn) and rice and may be derived therefrom. Modified starches (starch derivatives) have been chemically modified to allow the starch to function properly under conditions frequently encountered during processing or storage, such as high heat, high shear, low pH, etc. Modified starches are e.g. E-coded according to the international number system for food additives (INS(EG) 1400-1405, 1410, 1412-1414, 1420, 1422, 1440, 1442, 1443, 1450, 1451).

According to the invention, the starch component may be selected from starch, such as native starch, pregelatinized starch and starch derivatives e.g. such as defined above. Preferred starch derivatives are dextrin, acetylated starch, hydroxypropylated starch and phosphated starch. In a preferred embodiment, the starch component is native starch, such as corn (maize) starch.

The composition according to the invention preferably comprises the lactose component in an amount of 55-90% by weight, more preferably 60-90% by weight, more preferably 65-85% by weight, more preferably 65-75% by weight and even more preferably 68-72% by weight or 72-75% by weight, based on the total mass of the composition. The lactose component is preferably present in an amount of 68-72% by weight based on the total mass of the composition.

The cellulose component is preferably present in an amount of 5-30% by weight, more preferably 10-30% by weight, more preferably 15-25% by weight and even more preferably 19-22% by weight or 15-19% by weight, based on the total mass of the composition. The cellulose component is preferably present in an amount of 19-22% by weight based on the total mass of the composition.

The starch component may be comprised in the composition in an amount of 5-25% by weight, preferably 5-20% by weight, more preferably 8-13% by weight and even more preferably 8-12% by weight or 11-13% by weight, based on the total mass of the composition. The starch component may be comprised in the composition in an amount of preferably 8-12% by weight based on the total mass of the composition.

According to the present invention, addition of a lubricant is surprisingly not necessary to support the tabletting process. Thus, in a preferred embodiment, the present composition is substantially free of a lubricant.

In a preferred embodiment, the composition of the invention consists of at least one lactose component, at least one cellulose component and at least one starch component. More preferably, the composition consists of lactose monohydrate, microcrystalline cellulose and native starch, such as corn (maize) starch.

The compositions of the invention preferably have a total amount of water of less than 9% by weight, preferably 0.001-8% by weight, more preferably 0.001-7% by weight, more preferably 0.001-6.5% by weight and even more preferably 0.001-5.5% by weight, based on the total amount of the composition. The term "total amount of water" means the sum of molecularly complexed water (crystal water) plus free water.

In a preferred embodiment of the invention, the total amount of free water is less than 8% by weight, preferably 0.001-5% by weight and more preferably 0.001-3% by weight, based on the total amount of the composition, the amount of which is determined by the weight loss of the composition at a temperature of between 80° C. and 130° C.

The composition is preferably present in the form of agglomerates, such as granules, spheres, flakes or pellets, more preferably granules. The agglomerates of the present invention particularly have a spherical morphology or a spheroidal morphology. The agglomerates may have a mean particle size $d_{50}$ of 5-500 µm, preferably 50-250 µm. The composition and particularly the agglomerate of the present invention is substantially homogeneous, i.e. a substantially homogeneous mixture of the components of the composition. "Homogeneous mixture" or "homogeneous" as used herein means that the composition of the components is essentially constant over the whole agglomerate, i.e. the agglomerates of the invention do not exhibit any domains enriched by one of the components, e.g. a coating of a certain component.

During the tabletting process, the composition of the invention may be mixed with at least one pharmaceutically active component and optionally further excipients. Thus, in one aspect, the present invention provides a composition further comprising at least one pharmaceutically active component and optionally further excipients. Suitable pharmaceutically active components are particularly present in solid form and may be paracetamol, acetyl salicylic acid, ibuprofen, ketoprofen, diclofenac salts.

In another aspect, the composition, preferably the agglomerate, is free of a pharmaceutically active component.

Further excipients may be glidants, such as talcum; fillers, such as titanium dioxide and calcium diphosphate; binders, such as glucose, starch, gelatin, PVP; antistatic agents, such as aluminum oxide; surfactants, such as saponins; humectants, such as glycerol or PEG; glidants, such as silicon dioxide; and lubricants, such as magnesium stearate. More preferably, the excipients are selected from the group consisting of glidants, fillers, binders, antistatic agents, surfactants, and humectants as described above.

In a further aspect of the invention, a method for manufacturing a composition as described above is provided. The method of the invention comprises the steps of
(i) providing a solution or suspension comprising at least one lactose component, at least one cellulose component and/or at least one starch component in a liquid medium, and
(ii) spraying the solution or suspension obtained in step (i) in an environment at an increased temperature, optionally at reduced pressure, thereby removing the liquid medium at least partially.

In step (i), the at least one lactose component, the at least one cellulose component and the at least one starch component are preferably at least partially solved in a liquid medium, such as water, or an organic solvent, such as ethanol, acetic acid and acetone, and mixtures thereof.

The solution or suspension obtained in step (i) preferably has a total amount of lactose component, cellulose component and/or starch component in the range of between 5 and 60% by weight, more preferably 30-50% by weight, based on the total amount of solution or suspension.

The obtained solution or suspension is configured such that it may be pumped through spray nozzles having a diameter of 1.0 to 3.0 µm at a pressure of 0.5-100 bar and at a temperature of 20° C. at a rate of 10-3000 kg/h.

In step (ii), the solution or suspension obtained in step (i) is sprayed in an environment at an increased temperature of preferably 30-300° C., even more preferably 50-250° C. The pressure in the environment may be reduced to about 0-1.0 bar, preferably 0.003-0.4 bar. The spraying apparatus is configured such that in step (ii), the liquid medium is at least partially removed. The solution or suspension is preferably sprayed via nozzles, in particular one-substance or two-substance nozzles. In a preferred embodiment, the solution or suspension is pressed through a one-substance nozzle at a pressure of 10-100 bar, more preferably 30-60 bar, or pressed through a two-substance nozzle at a pressure of 0.5-5 bar, more preferably 1.5-3.5 bar.

In a preferred embodiment, the method according to the invention is conducted in a spray dryer, which is known in the field (e.g. type tall spray dryer).

In another embodiment, step (ii) may be conducted in the presence of particles of at least one of the cellulose component, the starch component or the lactose component, e.g. in a fluid bed granulator.

In a preferred embodiment, however, a process in a spray drier is performed, since this process is very cost-effective and the products obtained thereby result in the desired properties as described above.

In another aspect, the present invention relates to a product as obtained by the above described process.

In a further aspect, the present invention is directed to the use of a composition as described above as an excipient in making oral dosage forms, particularly as a tabletting excipient, more particularly as a direct tabletting excipient. Thus, in a further aspect, the present invention also provides an oral dosage form comprising a composition as described above and at least one pharmaceutically active component and optionally further excipients as described above. The oral dosage form of the invention may be configured for immediate release or for sustained release, particularly for immediate release. The oral dosage form of the invention may be in the form of a tablet, a capsule, a sachet, a granulate, preferably in the form of a tablet.

The composition of the invention may also be used in cosmetics, cleaning applications or engineering applications.

It has turned out that the use of the composition according to the invention as a (direct) tabletting excipient in standard tablet formulations results in a significant improvement of the tablet hardness and abrasion resistance compared to tablets in which the components of the composition according to the invention have been formulated as individual components, i.e. in a physical mixture. Simultaneously, the disintegration times have not been affected adversely in view of the increased hardness of the directly tableted dosage forms. The invention is further illustrated by the following figures and examples.

FIGURES

FIG. 1: Tablet hardness vs. compaction pressure: composition of the invention, MicroceLac and StarLac FIG. 2: Disintegration time vs. tablet hardness: composition of the invention, MicroceLac and StarLac FIG. 3: Disintegration time vs. compaction pressure: composition of the invention and physical mixtures FIG. 4: Hardness vs. compaction pressure in paracetamol-containing tablet: composition of the invention, MicroceLac and StarLac FIG. 5: Friability vs. compaction pressure in paracetamol-containing tablet: composition of the invention, MicroceLac and StarLac FIG. 6: Disintegration time vs. tablet hardness in paracetamol-containing tablet: composition of the invention, MicroceLac and StarLac FIG. 7: Paracetamol release vs. time: composition of the invention, MicroceLac and StarLac FIG. 8: SEM-image of agglomerates of the invention FIG. 9A+B: SEM-image of agglomerates according to Example 5

Figure 9A:
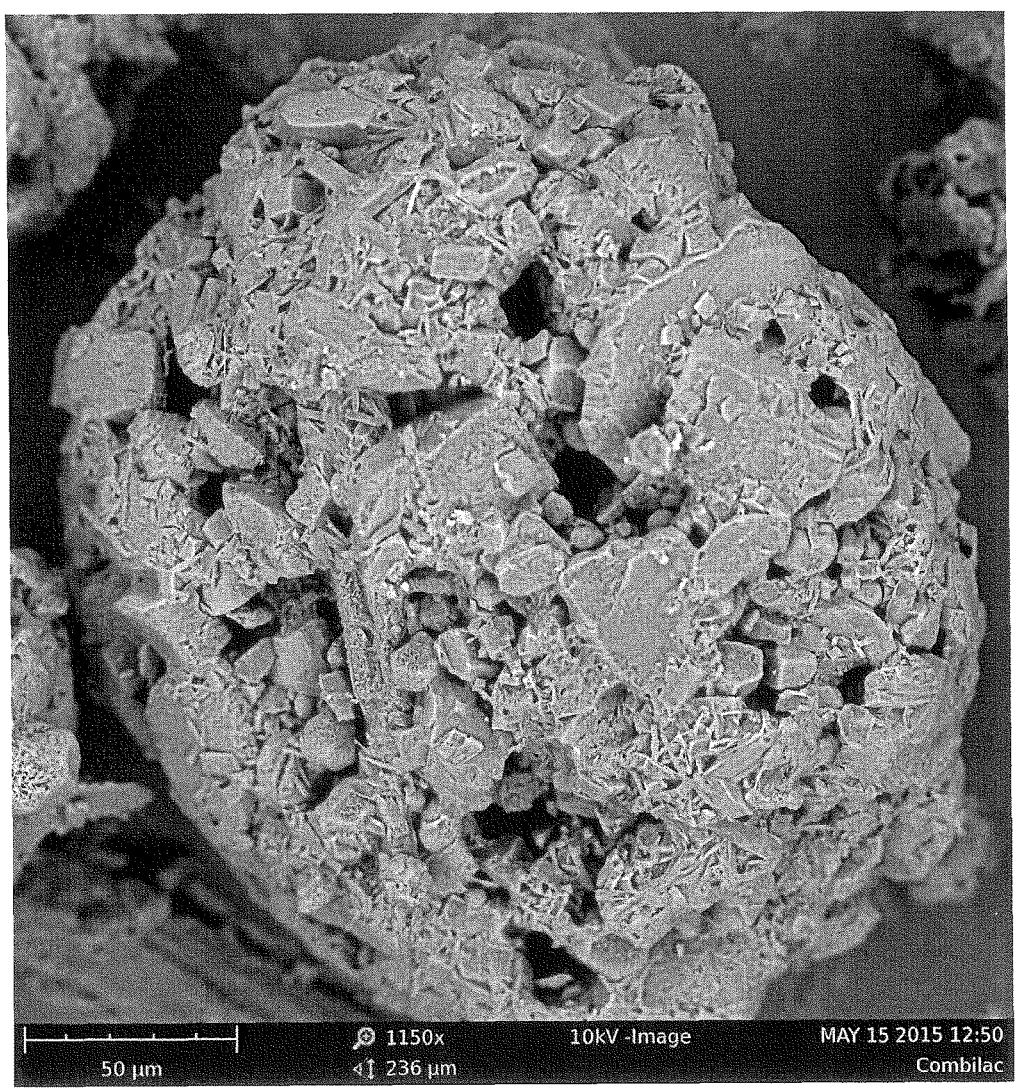
Figure 9B:
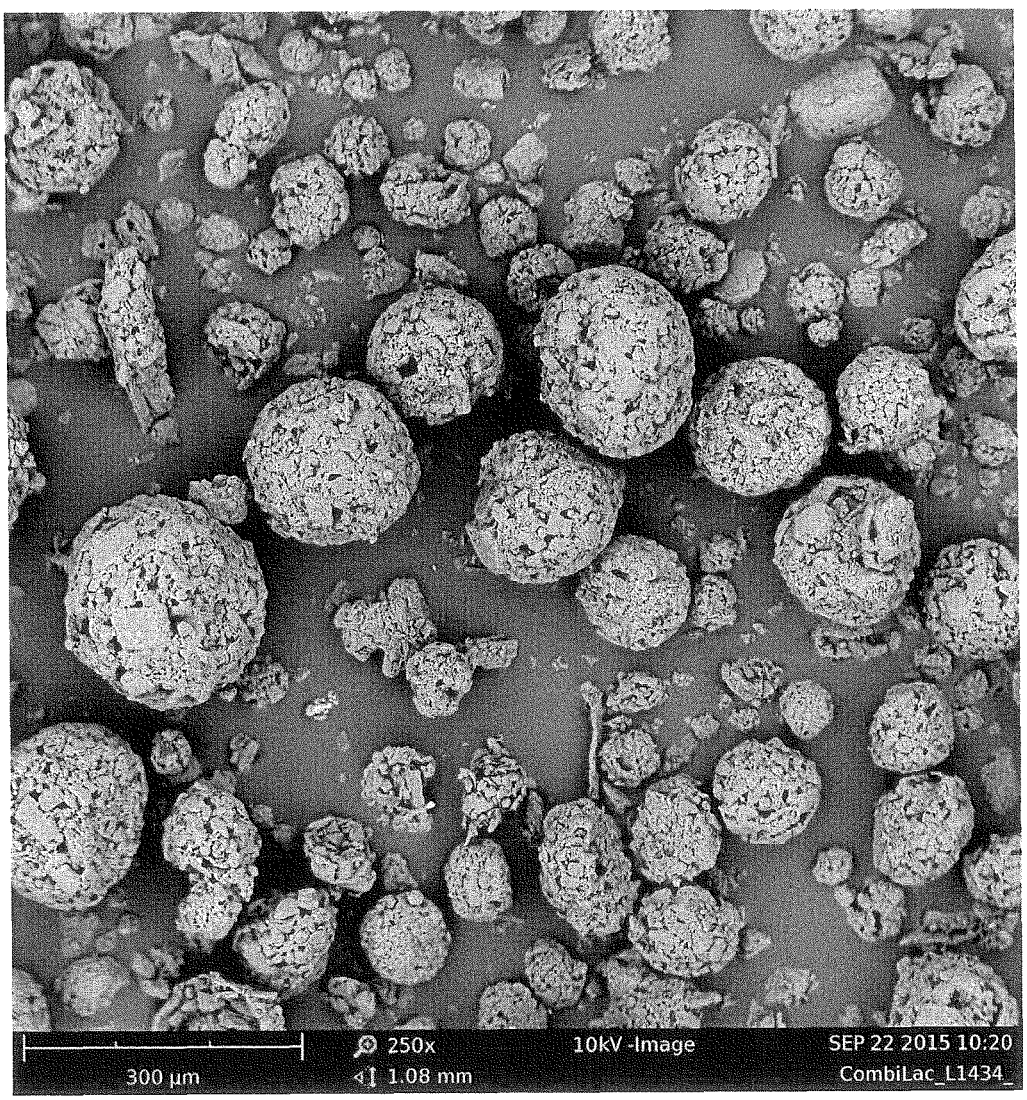
Figure 9C:
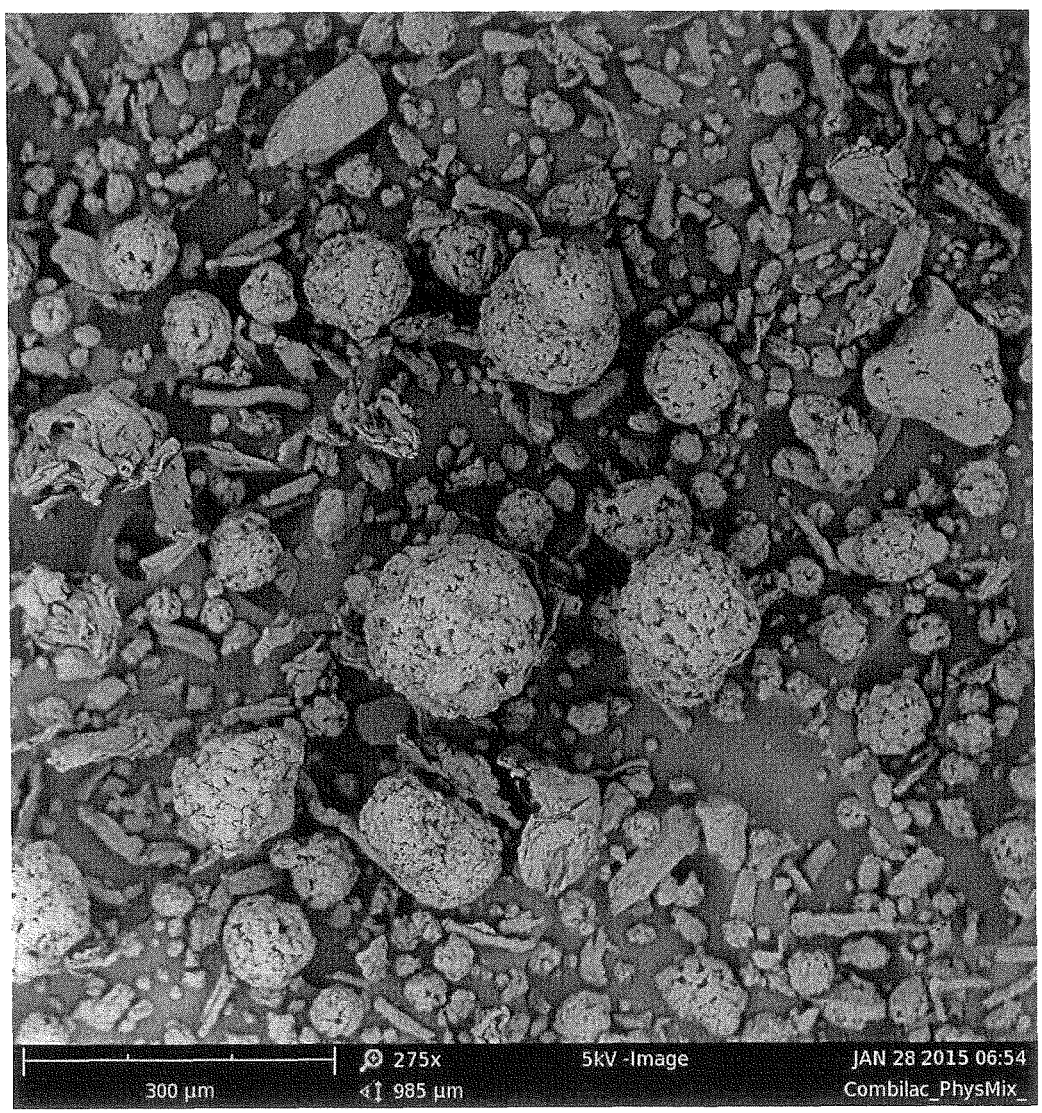

FIG. 9C: SEM-image of a physical mixture according to Example 5

Figure 10:
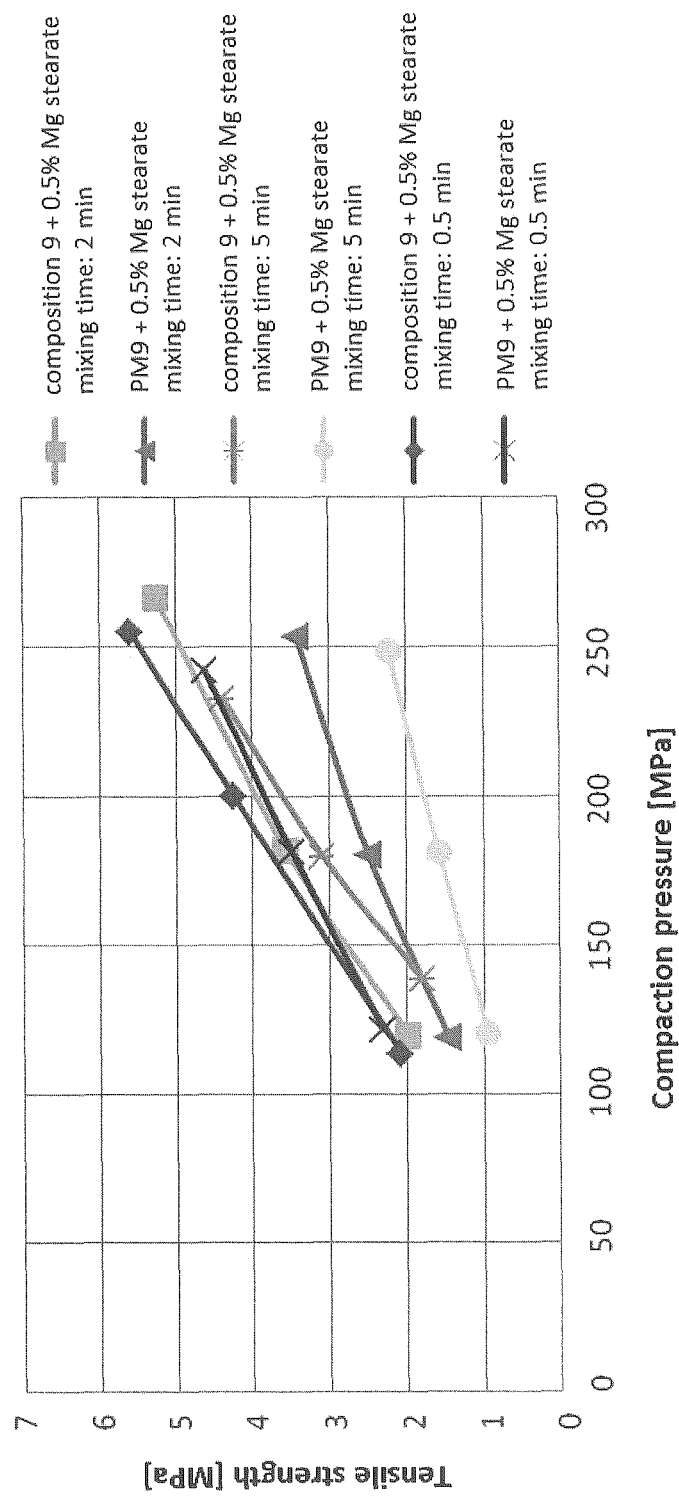

FIG. 10: Tensile strength vs. compaction pressure at different mixing times

Figure 11:
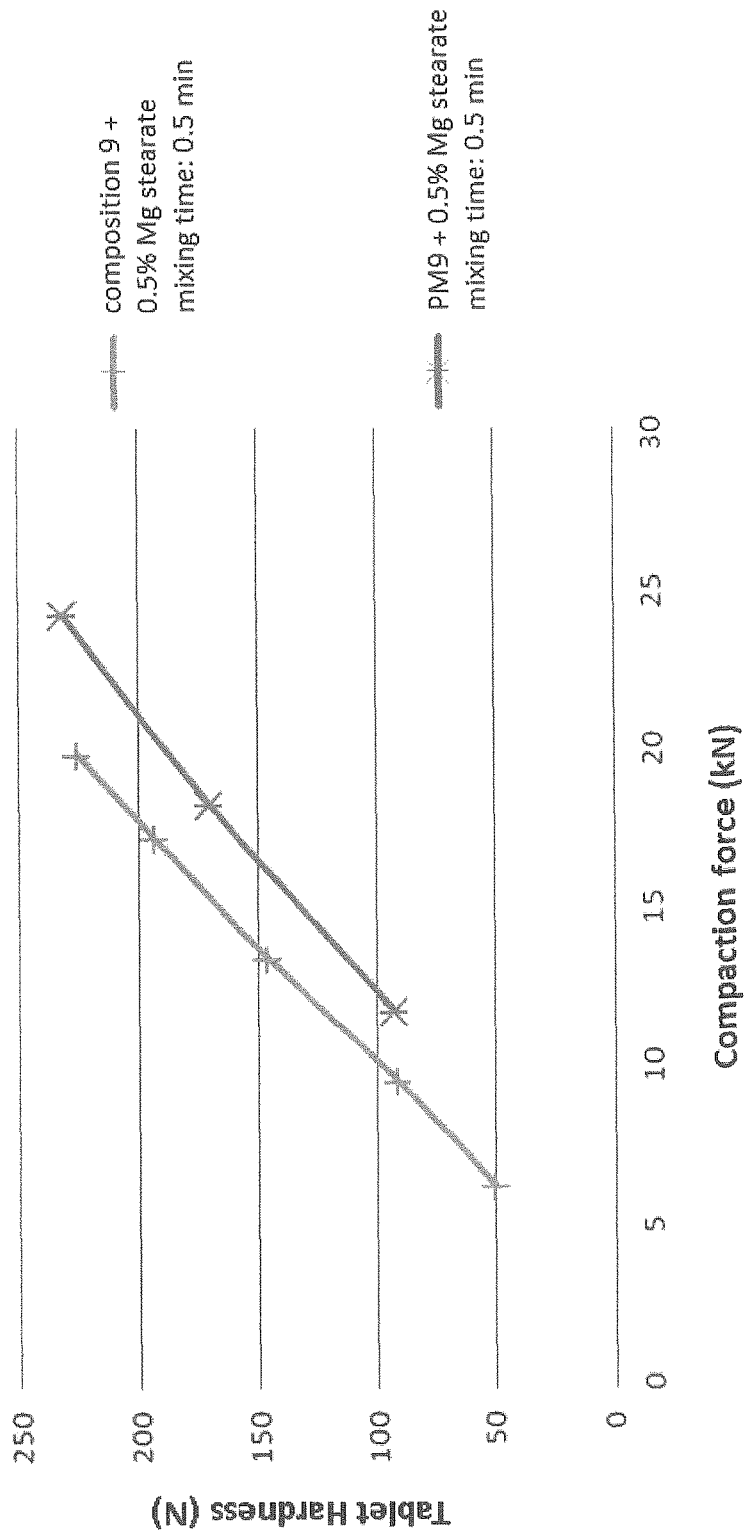

FIG. 11: Hardness vs. compaction force for composition 9 and PM9

EXAMPLES

Methods

Release times are determined using apparatus II (Erweka, Germany DT 808 LH). The tests take place in 1000 ml 0.01 HCl, 0.05 M phosphate buffer (pH 6.8) [produced according to the United States Pharmacopeial Convention (USP)] or acetate buffer (pH 4.5) [USP] at a rotation speed of 50 rpm. The quantitative measurement of the released active substance is carried out by means of UV spectroscopy.

Tablets were pressed on a Korsch apparatus EK 0 using punches having 7 mm (round), 8 mm (round) and 11 mm (round), providing tablets having a tablet weight of 150 mg, 240 mg or 500 mg, respectively.

Friability was tested according to Ph. Eur method on a Erweka friability tester.

Tablet hardness was tested with a Erweka TBH 425 tablet hardness tester.

Example 1 Tablets of the Invention

Composition 1 according to the invention was manufactured by spray-drying an aqueous suspension/solution (solid content: 40 wt.-%) containing lactose monohydrate, microcrystalline cellulose and native maize starch (see Table 1) in a spray-drying apparatus under the following conditions: water evaporation 1500 kg/h, inlet air temperature 165° C. and 40 bar dispersion pressure with one component nozzles. The obtained aggregates of the invention were mixed with magnesium stearate and tablets (8 mm, round, 240 mg) were pressed on a Korsch EK 0 apparatus. The composition of the tablets is indicated in Table 1.

For comparison, tablets were prepared from MicroceLac® and StarLac® using magnesium stearate as additional lubricant in the same manner as described above.

Figure 2:
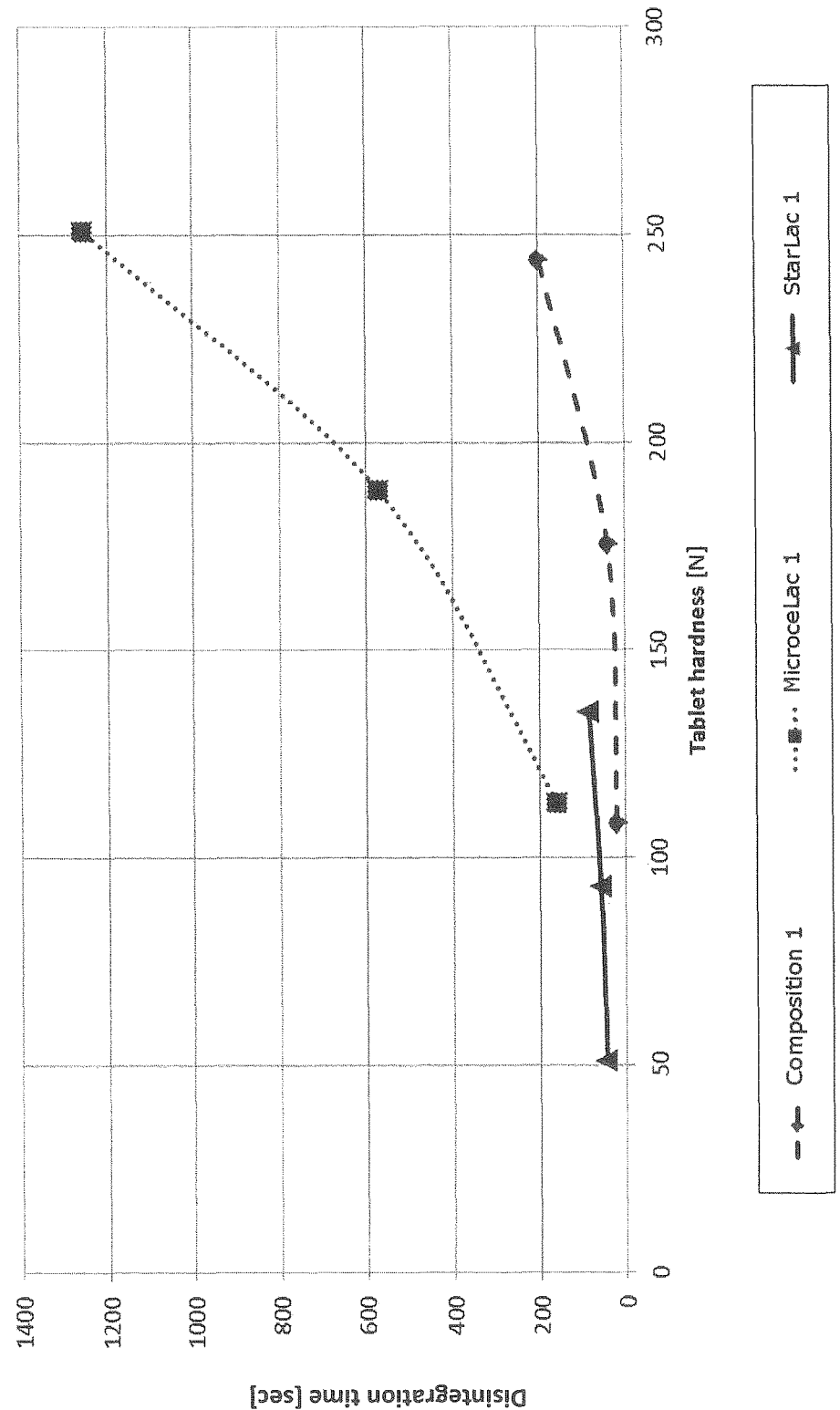

The tablet hardness was determined in relation to the respective compaction pressure used during tablet preparation. From FIG. 1, it can clearly be observed that the tablet hardness of the composition of the invention is comparable to the tablet hardness of MicroceLac®. MicroceLac® is known to provide excellent compactability and hardness. On the other hand, the tablets were subjected to a disintegration test. FIG. 2 shows the results of the disintegration time versus tablet hardness. It can be seen that despite the high tablet hardness of the tablets of the invention (>175N), the disintegration time is still below 200 seconds and thus comparable to the StarLac tablets. StarLac® is known as an excipient for short tablet disintegration times. From the results above, it can be seen that the tablets of the present invention synergistically combine the desirous characteristics of StarLac® and MicroceLac®, resulting in tablets having ideal hardness at excellent short disintegration times.

TABLE 1

Composition of tablets according to Example 1

| tablet | Composition 1 | MicroceLac 1 | StarLac 1 |
|---|---|---|---|
| Composition of invention [wt-%]: 70% lactose monohydrate, 20% microcrystalline cellulose, 10% native maize starch | 99.5 | — | — |
| MicroceLac ® 100 [wt-%]: 75% α-lactose monohydrate 25% microcrystalline cellulose | — | 99.5 | — |
| StarLac ® [wt-%]: 85% α-lactose monohydrate 15% native maize starch | — | — | 99.5 |
| magnesium stearate | 0.5 | 0.5 | 0.5 |

Further compositions (compositions 2-4) were made under the conditions as described above. Tablets were pressed in the same manner as described above. The compositions and test results of the tablets are shown in Table 2.

TABLE 2

Compositions 2-3

| | | Composition 2 | Composition 3 |
|---|---|---|---|
| 80% lactose monohydrate 12.5% microcrystalline cellulose 7.5% native maize starch [wt-%] | | 99.5 | — |
| 60% lactose monohydrate 25.5% microcrystalline cellulose 12.5% native maize starch [wt-%] | | — | 99.5 |
| magnesium stearate [wt.-%] | | 0.5 | 0.5 |
| Tablet hardness [N] at compaction force | 6 kN | 70 | 170 |
| | 9 kN | 93 | 249 |
| | 13 kN | 122 | 311 |
| disintegration time (s) at compaction force | 6 kN | 26 | 48 |
| | 9 kN | 22 | 178 |
| | 13 kN | 15 | 315 |

All tablets shown in Table 2 have good hardness at acceptable disintegration times.

Figure 8:
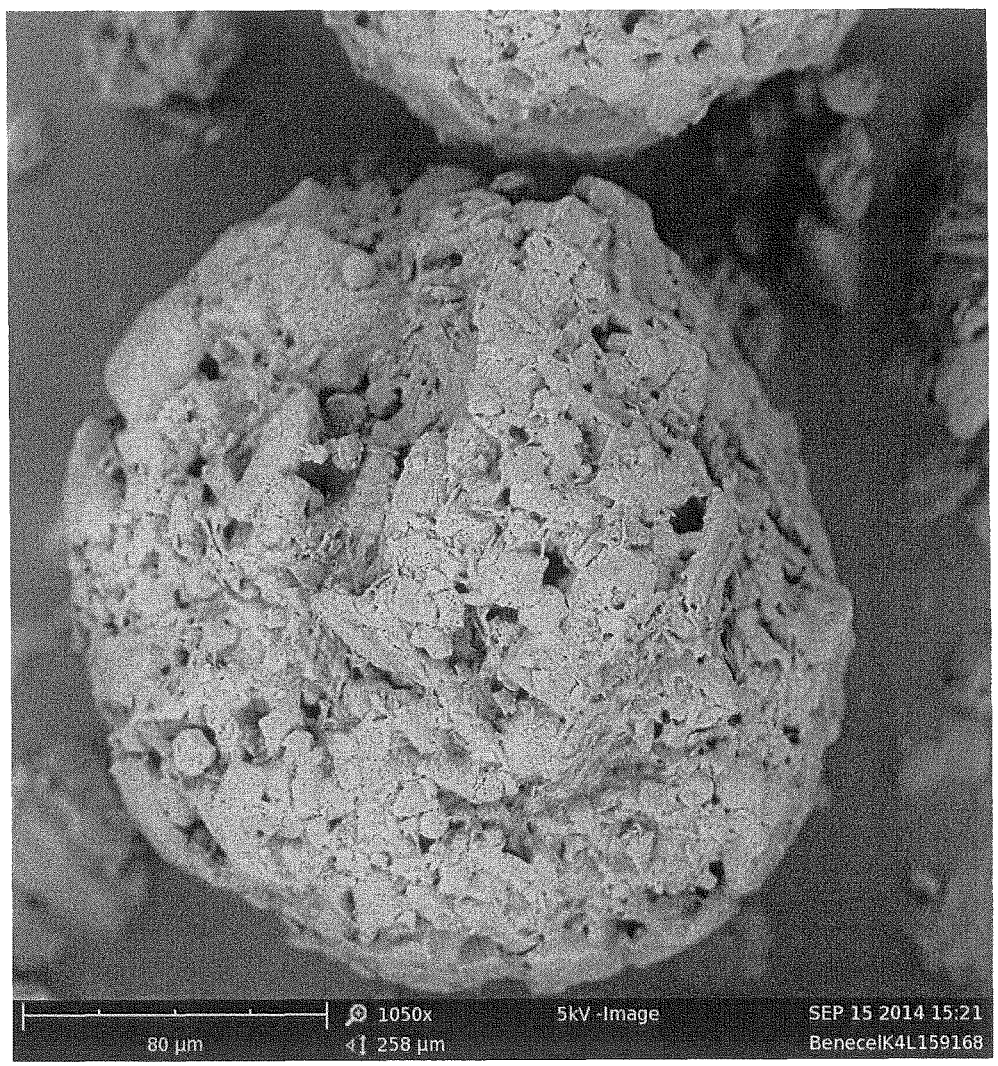

FIG. 8 shows a representative SEM-image of an agglomerate of the compositions according to the invention. Also from the SEM image of complete and broken agglomerates it can be derived that the agglomerates represent a homogeneous mixture.

Example 2 Physical Mixtures

In order to compare the tablets according to the invention with tablets produced from physical mixtures, tablets (7 mm, round, 150 mg) were pressed on a Korsch EKO apparatus. The physical mixtures were homogeneously mixed on a turbula blender, Willy A. Bachofen Maschinenfabrik, Muttenz, Swiss before tabletting. The composition of the tablets is shown in Table 3.

TABLE 3

Comparison of composition of the invention and physical mixtures

| | Composition 5 | Composition 6 | PM 5 | PM 6 |
|---|---|---|---|---|
| composition of the invention: 70% lactose monohydrate 20% microcrystalline cellulose 10% native maize starch [wt-%] | 99.5 | 96.5 | — | — |
| lactose monohydrate [wt-%] | — | — | 69.65 | 67.55 |
| microcrystalline cellulose [wt-%] | — | — | 19.9 | 19.3 |
| native maize starch [wt-%] | — | — | 9.95 | 9.65 |
| magnesium stearate [wt-%] | 0.5 | 0.5 | 0.5 | 0.5 |
| sodium croscarmellose [wt-%] | — | 3 | — | 3 |

Figure 3:
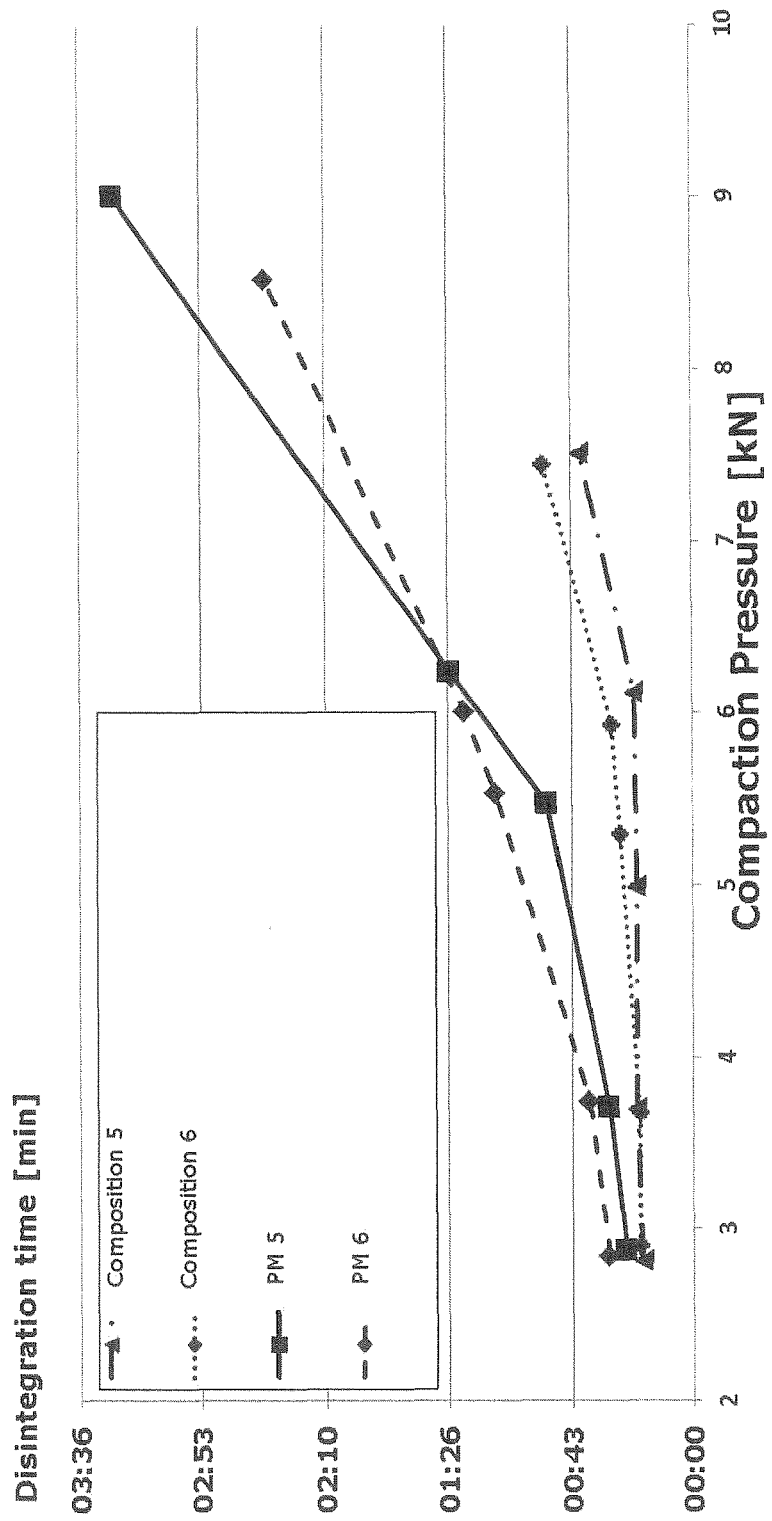

The disintegration times in water at 37° C. of the obtained tablets were determined. The data are illustrated in FIG. 3. FIG. 3 shows that the tablets of the present invention (compositions 5 and 6) in each case have significantly reduced disintegration time as compared to the tablets prepared from the physical mixture (PM).

Example 3 Drug-containing Tablets

Paracetamol-containing tablets (11 mm, round, 500 mg) were prepared on a Korsch EK 0. The composition of the tablets is indicated in Table 4.

TABLE 4

Composition of drug-containing tablets

| | Composition 7 | MicroceLac 7 | StarLac 7 |
|---|---|---|---|
| composition of the invention: 70% lactose monohydrate 20% microcrystalline cellulose 10% native maize starch [wt-%] | 88 | — | — |
| StarLac ® [wt-%] | — | — | 88 |
| MicroceLac ® [wt-%] | — | 88 | — |
| magensium stearate [wt-%] | 1 | 1 | 1 |
| Aerosil [wt-%] | 1 | 1 | 1 |
| paracetamol [wt-%] | 10 | 10 | 10 |

Figure 4:
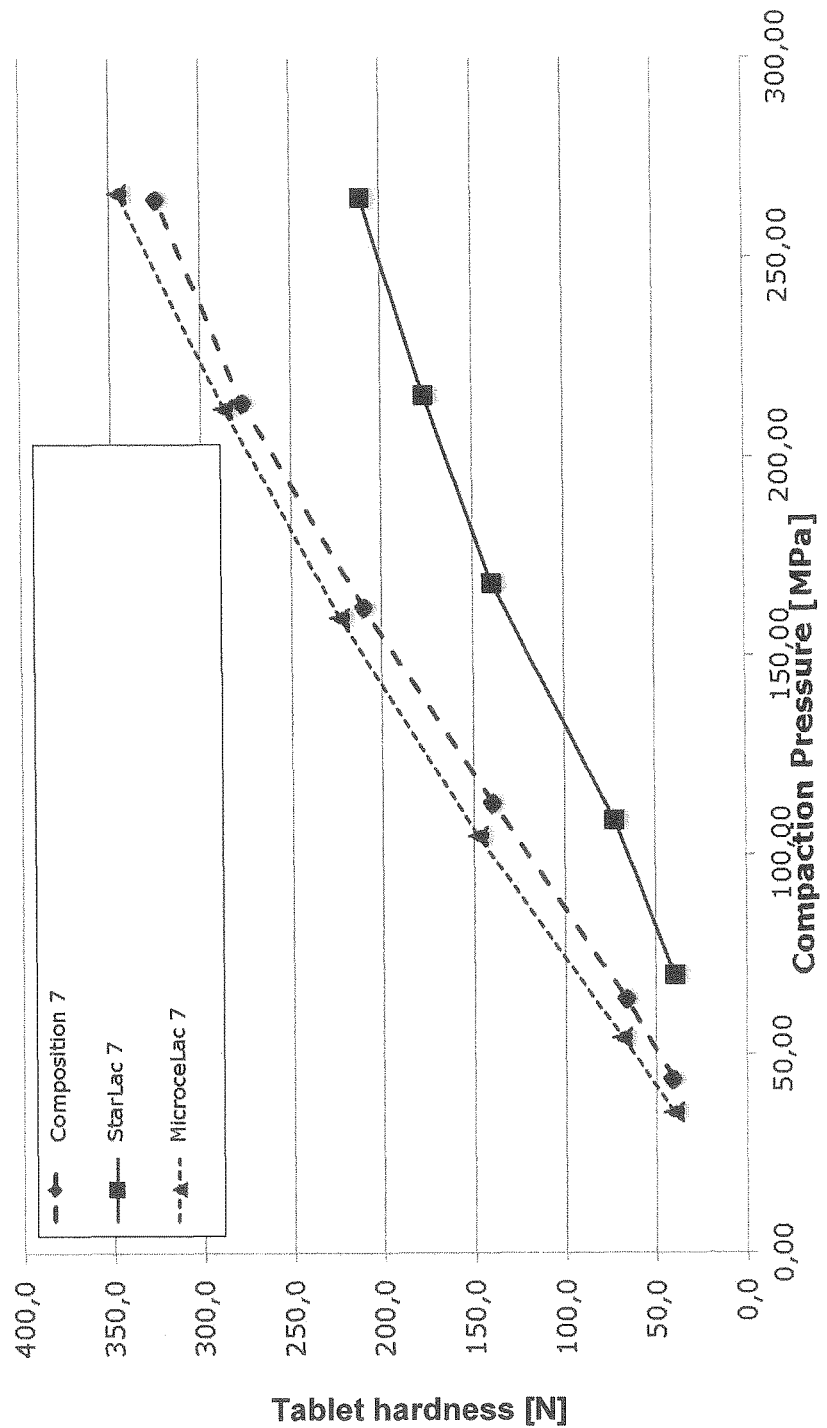
Figure 5:
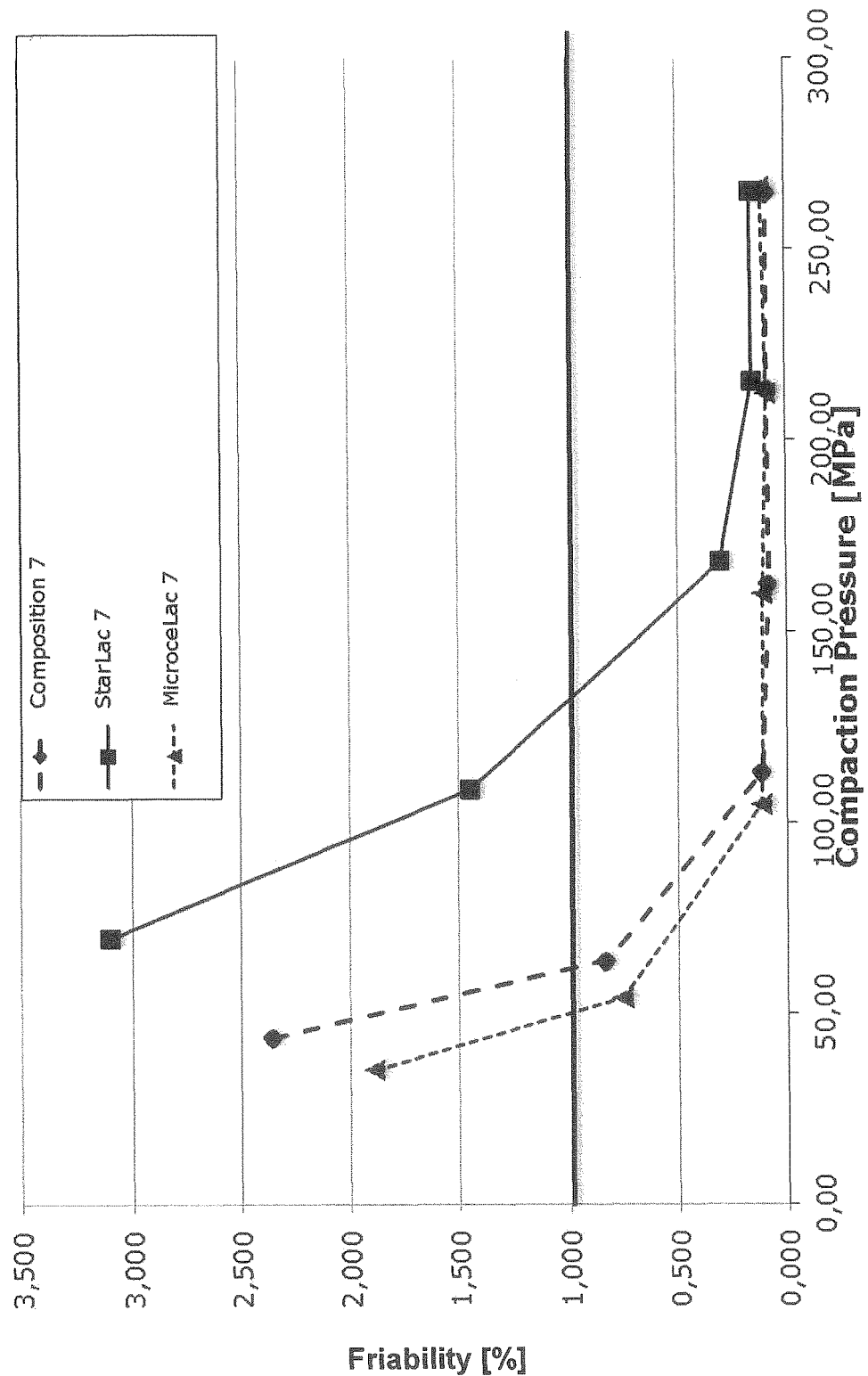
Figure 6:
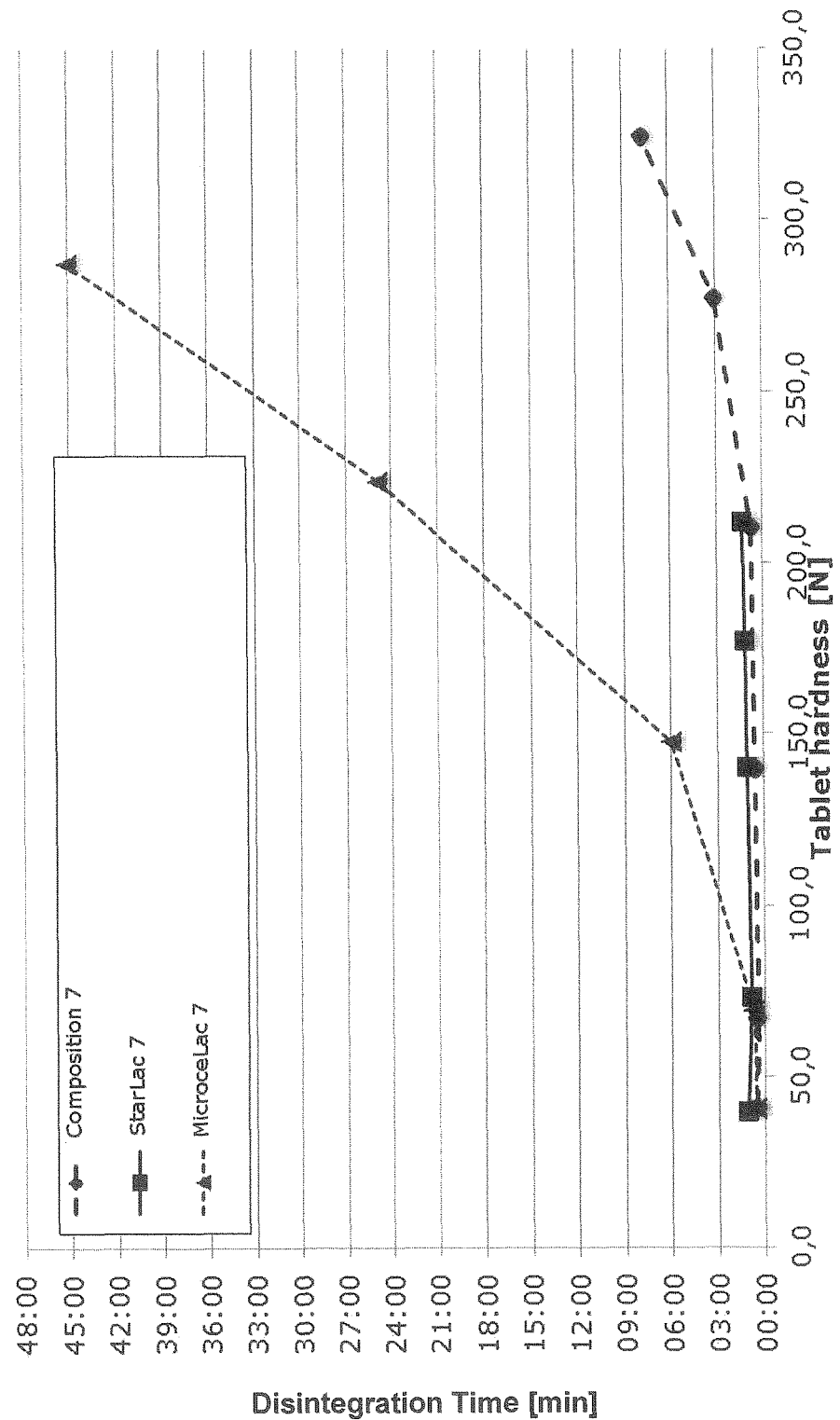
Figure 7:
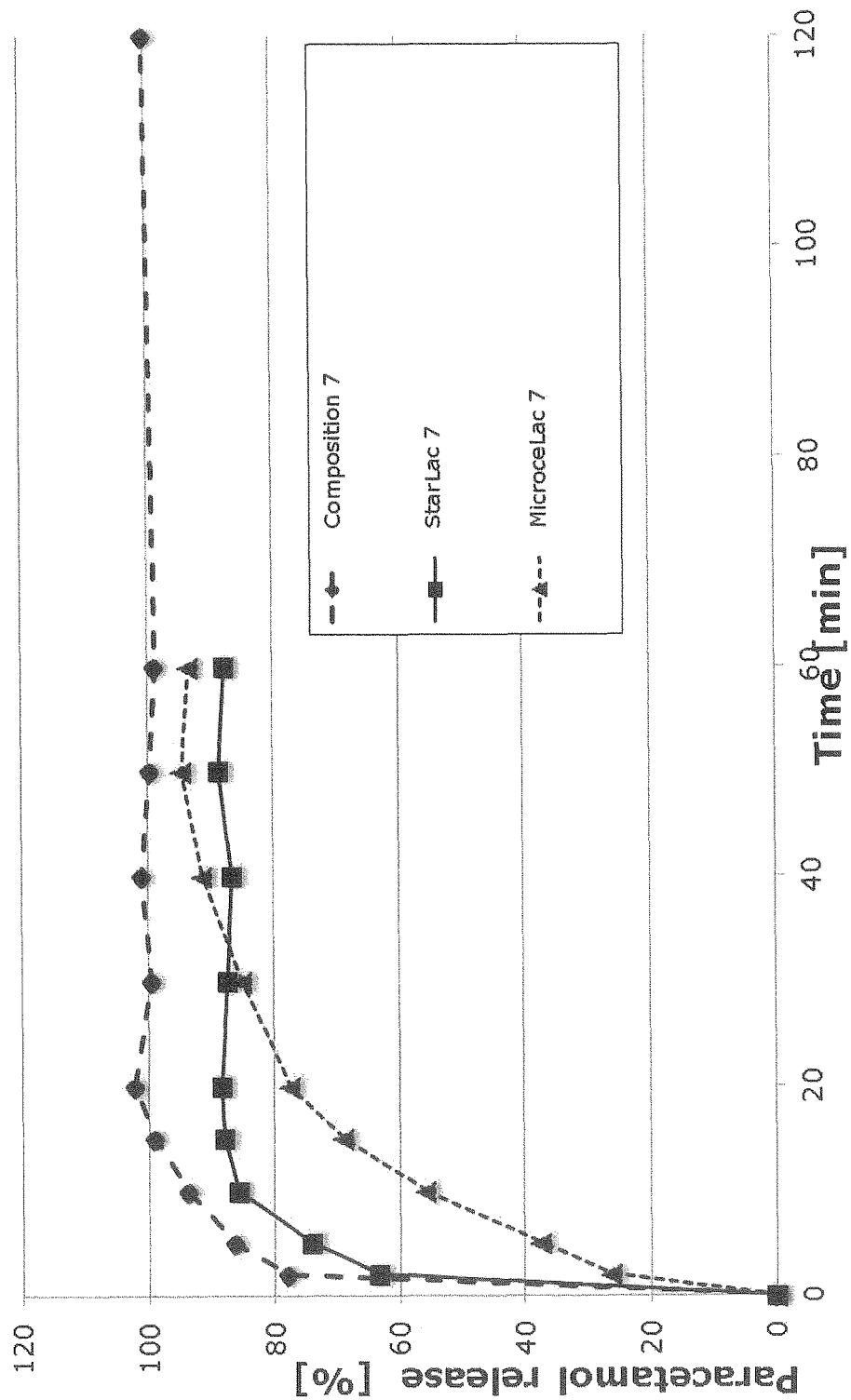

The results in Example 1 also apply to the tablets of the invention containing an active ingredient such as paracetamol. As can be seen from FIGS. 4-7, the tablet hardness and friability of the tablets according to the invention are comparable to those of the MicroceLac tablet (which is known to have excellent hardness and friability characteristics) (FIGS. 4 and 5). On the other hand, however, the disintegration time of the tablets according to the invention is comparable to the disintegration rate of the StarLac tablet (which is known to have excellent disintegration characteristics) (FIG. 6). The release of paracetamol over time is indicated in FIG. 7. The graph shows the fastest release time for the tablets of the invention (composition 7) as compared to the reference tablets (MicroceLac 7 and StarLac 7). This release profile makes the compositions of the invention ideally suitable for immediate release applications.

Example 4 Tablets with Higher Amounts of Active Agent

Tablets (11 mm, round, 500 mg) containing paracetamol (30%) as a pharmaceutically active component were prepared on a Korsch EKO apparatus. The composition of the tablets is indicated in Table 5.

TABLE 5

Tablets containing 30% of paracetamol

|  |  | Composition 8 | MicroceLac 8 | StarLac 8 |
|---|---|---|---|---|
| composition of the invention: 70% lactose monohydrate 20% microcrystalline cellulose 10% native maize starch [wt-%] |  | 68.5 | — | — |
| StarLac ® [wt-%] |  | — | — | 68.5 |
| MicroceLac ® [wt-%] |  | — | 68.5 | — |
| magnesium stearate |  | 1 | 1 | 1 |
| Aerosil [wt-%] |  | 0.5 | 0.5 | 0.5 |
| paracetamol [wt-%] |  | 30 | 30 | 30 |
| tablet hardness (N) at compaction force [kN] | 7 kN | 52 | 51 | — |
|  | 13 kN | 90 | 104 | — |
|  | 19 kN | 115 | 133 | — |
| Friability (%) at compaction force [kN] | 7 kN | 2.5 | 1.8 | — |
|  | 13 kN | 0.5 | 0.2 | — |
|  | 19 kN | 5.4 | 2.4 | — |
| disintegration time [min] at compaction force [kN] | 7 kN | 0:44 | 2:04 | — |
|  | 13 kN | 0:44 | 25:32 | — |
|  | 19 kN | 1:25 | >60 | — |

While the StarLac 8 tablets have high and thus unacceptable friability at any compaction force, the results in Table 5 clearly show that the tablets according to the invention have an acceptable hardness (>90 N), acceptable friability (<1%) and acceptable short disintegration times (<1 min) at a compaction force of 13 kN. The tablets containing MicroceLac (MicroceLac 8) have an acceptable hardness (104 N). However, these tablets provide long and unacceptable disintegration times (>25 min).

Example 5 Morphological Observations

In order to investigate the morphological properties, agglomerates according to the invention were made of 70% lactose monohydrate, 20% microcrystalline cellulose and 10% native maize starch. The agglomerate according to the invention was manufactured by spray-drying an aqueous suspension/solution (solid content 40 wt.-%) in a spray-drying apparatus under the following conditions: water evaporation 1,500 kg/h, inlet air temperature 165° C. and 40 bar dispersion pressure with one component nozzles (composition 9). For comparison, a physical mixture made of 70% spray-dried lactose monohydrate, 20% microcrystalline cellulose and 10% native maize starch was compounded in a turbula blender, Willy A. Bachofen Maschinenfabrik, Muttenz, Switzerland (PM9). The SEM-micrographs of the agglomerate according to the invention (FIGS. 9A and B) and the physical mixture (FIG. 9C) are illustrated in the Figures. In the agglomerate according to the invention, all compounds together form homogeneous sphericals and cannot be separated by physical processes. Therefore, the predetermined concentration of the components in the composition can be ensured at any time during delivery. In the physical mixture, the components lactose, cellulose and starch are separated from each other (FIG. 9C). Due to the different sizes and characteristics of the compounds, at least a partial segregation of the components might occur, which makes it impossible to deliver several portions having the same composition.

Example 6

In a further step, 0.5 wt.-% magnesium stearate were added to composition 9 and the physical mixture PM9 prepared in Example 5. Composition 9 and PM9, respectively, were mixed with magnesium stearate at different mixing times (0.5, 2.0 and 5.0 minutes). From the magnesium stearate containing compound 9 and the magnesium stearate containing physical mixture PM9, tablets were pressed on a Korsch EKO apparatus (8 mm, round, 240 mg). The tablets were compacted at different compaction pressures. In FIG. 10, the tensile strength is shown over the compaction pressure. The data show that the agglomerates according to the invention (composition 9) are far less sensitive to the mixing procedure than the physical mixture.

In FIG. 11, the tablet hardness is shown over the compaction force. The results evidence that the compressibility of tablets containing composition 9 is improved over tablets containing a physical mixture.

The following items further describe the present invention:

1. Composition comprising at least one lactose component, at least one cellulose component and at least one starch component.
2. Composition according to item 1, wherein the lactose component is selected from anhydrous lactose and lactose monohydrate.
3. Composition according to item 1 or 2, wherein the cellulose component is selected from cellulose, such as microcrystalline cellulose (MCC), and powder cellulose; and cellulose derivatives, such as hypromellose (hydroxypropylmethylcellulose (HPMC)), hydroxypropylcellulose (HPC), hydroxyethylcellulose (HEC), carboxymethylcellulose (CMC), carboxyethylcellulose (CEC), ethylcellulose (EC), hypromellosephthalate, and salts thereof.
4. Composition according to any of items 1-3, wherein the starch component is selected from starch, such as native starch, pregelatinized starch and starch derivatives, particularly native starch.
5. Composition according to any of items 1-4, wherein the lactose component is present in an amount of 55-90% by weight, more preferably 60-90% by weight, more preferably 65-85% by weight, more preferably 65-75% by weight and even more preferably 68-72% by weight or 72-75% by weight, based on the total mass of the composition.
6. Composition according to any of items 1-5, wherein the cellulose component is present in an amount of 5-30% by weight, preferably 10-30% by weight, more preferably 15-25% by weight and even more preferably 19-22% by weight or 15-19% by weight, based on the total mass of the composition.
7. Composition according to any of items 1-6, wherein the starch component is present in an amount of 5-25% by weight, preferably 5-20% by weight, more preferably 8-13% by weight, and even more preferably 8-12% by weight or 11-13% by weight, based on the total mass of the composition.
8. Composition according to any of items 1-7, wherein the composition consists of at least one lactose component, at least one cellulose component and at least one starch component.
9. Composition according to any of items 1-8, wherein the composition consists of lactose monohydrate, microcrystalline cellulose and native starch.
10. Composition according to any of items 1-9, wherein the composition is substantially free of a lubricant.
11. Composition according to any of items 1-10 having a total amount of water of less than 9% by weight, preferably 0.001-8% by weight, more preferably 0.001-7% by weight, more preferably 0.001-6.5% by weight and even more preferably 0.001-5.5% by weight, based on the total amount of the composition.

12. Composition according to any of items 1-11 having a total amount of free water of less than 8% by weight, preferably 0.001-5% by weight, more preferably 0.001-3% by weight, based on the total amount of the composition.

13. Composition according to any of items 1-12, wherein the composition is in the form of agglomerates, such as granules, particularly having a mean particle size $d_{50}$ of 5-500 μm, preferably 50-250 μm.

14. Composition according to item 13, wherein the agglomerate represents an homogeneous mixture of the components of the composition.

15. Composition according to any of items 13 or 14, wherein the agglomerate has a spherical morphology or a spheroidal morphology.

16. Composition according to any of items 1-15 further comprising at least one pharmaceutically active component and optionally further excipients.

17. Composition according to item 16, wherein the excipients are selected from the group consisting of glidants, fillers, binders, antistatic agents, surfactants, humectants and lubricants.

18. Method for manufacturing a composition according to any of items 1-17 comprising the steps of
   (i) providing a solution or suspension comprising at least one lactose component, at least one cellulose component and/or at least one starch component in a liquid medium, and
   (ii) spraying the solution or suspension obtained in step (i) in an environment at an increased temperature, optionally at reduced pressure, thereby removing the liquid medium at least partially.

19. Method according to item 18, wherein the liquid medium is selected from water, organic solvents such as ethanol, acetic acid and acetone, and mixtures thereof.

20. Method according to any of items 18 or 19, wherein the total amount of lactose component, cellulose component and/or starch component is in the range of between 5 and 60% by weight, preferably 30-50% by weight, based on the total amount of the solution or suspension.

21. Method according to any of items 18-20, wherein the temperature in step (ii) is in the range of 30-300° C., preferably about 50-250° C.

22. Method according to any of items 18-21, wherein spraying in step (ii) is performed through nozzles, particularly one-substance or two-substance nozzles.

23. Method according to any of items 18-22, wherein the pressure in step (ii) is in the range of 0 to 1.0 bar, preferably 0 to 0.5 bar, more preferably 0.003 to 0.4 bar.

24. Method according to any of items 18-23 which is conducted in a spray dryer.

25. Method according to any of items 18-24, wherein step (ii) is conducted in the presence of particles of at least one of the cellulose component, the starch component or the lactose component.

26. Method according to item 25 which is conducted in a fluid bed granulator.

27. Use of a composition according to any of claims 1-17 as an excipient in making oral dosage forms, particularly as a tabletting excipient, more particularly as a direct tabletting excipient.

28. Use of the composition according to any of claims 1-17 in cosmetics, cleaning applications or engineering.

29. Oral dosage form comprising a composition according to any of claims 1-17, at least one pharmaceutically active component, and optionally further excipients.

30. Oral dosage form according to claim 29 for immediate release.

31. Oral dosage form according to any of claim 29 or 30, which is a tablet, a capsule, a sachet or a granulate.

The invention claimed is:

1. Agglomerate consisting of at least one lactose component, at least one cellulose component and at least one starch component, and optionally water, and when water is present, the water is present in an amount of less than 9% by weight, based on a total amount of the agglomerate.

2. Agglomerate according to claim 1, wherein the lactose component is selected from anhydrous lactose and lactose monohydrate.

3. Agglomerate according to claim 1, wherein the cellulose component is selected from cellulose, microcrystalline cellulose (MCC) and powder cellulose; and cellulose derivatives, hypromellose (hydroxypropylmethylcellulose (HPMC)), hydroxypropyl cellulose (HPC), hydroxyethylcellulose (HEC), carboxymethylcellulose (CMC), carboxyethylcellulose (CEC), ethylcellulose (EC), hypromellosephthalate and salts thereof.

4. Agglomerate according to claim 1, wherein the starch component is selected from starch, native starch, pregelatinized starch, and starch derivatives.

5. Agglomerate according to claim 1, wherein water is present in a total amount of water of less than 9% by weight, based on a total amount of the agglomerate.

6. Agglomerate according to claim 1, wherein the agglomerate is in the form of granules having a mean particle size $d_{50}$ of 5-500 μm.

7. Agglomerate according to claim 6, in the form of a homogeneous mixture of all components.

8. An oral dosage comprising the agglomerate according to claim 1, at least one pharmaceutically active component and optionally one or more further excipients, wherein said oral dosage is free of any lubricants.

9. Method for manufacturing an agglomerate according to claim 1 comprising the steps of
   (i) providing a solution or suspension comprising at least one lactose component, at least one cellulose component and at least one starch component in a liquid medium, and
   (ii) spraying the solution or suspension obtained in step (i) in an environment at an increased temperature, optionally at reduced pressure, thereby removing the liquid medium at least partially.

10. Method according to claim 9, wherein the liquid medium is selected from water, an organic solvent, and mixtures thereof.

11. Method according to claim 9, which is conducted in a spray dryer.

12. A method of using the agglomerate according to claim 1, said method comprising:
   incorporating the agglomerate into a formulation (i) as an excipient in making oral dosage forms, (ii) as a tabletting excipient, or (iii) as a direct tabletting excipient.

13. Oral dosage form consisting of an agglomerate according to claim 1, at least one pharmaceutically active component, and optionally further excipients selected from talcum, titanium dioxide, calcium diphosphate, gelatin, aluminum oxide, saponins, and humectants.

14. Agglomerate according to claim 5, having a total amount of water of 0.001-5.5% by weight, based on the total amount of the agglomerate.

15. Agglomerate according to claim 6, wherein the agglomerate is in the form of granules having a mean particle size $d_{50}$ of 50-250 μm.

16. Method according to claim 9, wherein the liquid medium is an organic solvent comprising ethanol, acetic acid, acetone, or a mixture thereof.

17. A method of using the agglomerate according to claim 14, said method comprising:
incorporating the agglomerate into a formulation (i) as an excipient in making oral dosage forms, (ii) as a tabletting excipient, or (iii) as a direct tabletting excipient.

18. Oral dosage form consisting of an agglomerate according to claim 14, at least one pharmaceutically active component, and optionally further excipients selected from talcum, titanium dioxide, calcium diphosphate, gelatin, aluminum oxide, saponins, humectants, and magnesium stearate.

19. Agglomerate according to claim 4, wherein the starch derivatives comprise dextrin, acetylated starch, hydroxypropylated starch, and phosphate starch.

20. An oral dosage consisting of the agglomerate according to claim 14 and at least one pharmaceutically active component.

\* \* \* \* \*